(12) United States Patent
Yoo et al.

(10) Patent No.: US 9,311,431 B2
(45) Date of Patent: Apr. 12, 2016

(54) SECONDARY TARGET DESIGN FOR OPTICAL MEASUREMENTS

(71) Applicant: KLA-Tencor Corporation, Milpitas, IA (US)

(72) Inventors: Sungchul Yoo, Campbell, CA (US); Andrei V. Shchegrov, Campbell, CA (US); Thaddeus G. Dziura, San Jose, CA (US); InKyo Kim, Cupertino, CA (US); SeungHwan Lee, Suwon-si (KR); ByeoungSu Hwang, Milpitas, CA (US); Leonid Poslavsky, Belmont, CA (US)

(73) Assignee: KLA-Tencor Corporation, Milpitas, CA (US)

(*) Notice: Subject to any disclaimer, the term of this patent is extended or adjusted under 35 U.S.C. 154(b) by 673 days.

(21) Appl. No.: 13/665,436

(22) Filed: Oct. 31, 2012

(65) Prior Publication Data

US 2013/0116978 A1 May 9, 2013

Related U.S. Application Data

(60) Provisional application No. 61/555,108, filed on Nov. 3, 2011.

(51) Int. Cl.
| | |
|---|---|
| *G06F 17/40* | (2006.01) |
| *G06F 19/00* | (2011.01) |
| *G06F 17/50* | (2006.01) |
| *G06F 17/10* | (2006.01) |
| *G01N 21/956* | (2006.01) |
| *G03F 7/20* | (2006.01) |
| *G01N 21/47* | (2006.01) |

(52) U.S. Cl.
CPC ............. *G06F 17/50* (2013.01); *G01N 21/47* (2013.01); *G01N 21/956* (2013.01); *G03F 7/70625* (2013.01); *G03F 7/70683* (2013.01); *G06F 17/10* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | | |
|---|---|---|---|---|
| 5,607,800 | A * | 3/1997 | Ziger | 430/8 |
| 5,739,909 | A * | 4/1998 | Blayo et al. | 356/369 |
| 5,867,276 | A * | 2/1999 | McNeil et al. | 356/445 |
| 5,889,593 | A | 3/1999 | Bareket | |
| 5,963,329 | A * | 10/1999 | Conrad et al. | 356/613 |
| 6,429,943 | B1 * | 8/2002 | Opsal et al. | 356/625 |
| 6,721,691 | B2 * | 4/2004 | Bao | G01N 21/956 356/369 |
| 6,813,034 | B2 | 11/2004 | Rosencwaig et al. | |
| 6,819,426 | B2 | 11/2004 | Sezginer et al. | |
| 7,127,363 | B2 * | 10/2006 | Loyer | 702/57 |
| 7,349,079 | B2 | 3/2008 | Zhao et al. | |
| 7,417,750 | B2 * | 8/2008 | Vuong et al. | 356/636 |

(Continued)

*Primary Examiner* — Edward Cosimano
(74) *Attorney, Agent, or Firm* — Suiter Swantz pc llo

(57) ABSTRACT

The disclosure is directed to improving optical metrology for a sample with complex structural attributes utilizing custom designed secondary targets. At least one parameter of a secondary target may be controlled to improve sensitivity for a selected parameter of a primary target and/or to reduce correlation of the selected parameter with other parameters of the primary target. Parameters for the primary and secondary target may be collected. The parameters may be incorporated into a scatterometry model. Simulations utilizing the scatterometry model may be conducted to determine a level of sensitivity or a level of correlation for the selected parameter of the primary target. The controlled parameter of the secondary target may be modified until a selected level of sensitivity or a selected level of correlation is achieved.

32 Claims, 4 Drawing Sheets

(56) References Cited

U.S. PATENT DOCUMENTS

| | | | |
|---|---|---|---|
| 7,465,590 B1 | 12/2008 | Feng et al. | |
| 7,478,019 B2* | 1/2009 | Zangooie et al. | 703/2 |
| 7,522,295 B2* | 4/2009 | Vuong et al. | 356/636 |
| 7,667,858 B2* | 2/2010 | Chard et al. | 356/625 |
| 8,062,910 B1 | 11/2011 | Feng et al. | |
| 8,090,558 B1 | 1/2012 | Dziura | |
| 2003/0187602 A1* | 10/2003 | Bao et al. | 702/94 |
| 2003/0197872 A1* | 10/2003 | Littau et al. | 356/625 |
| 2005/0240361 A1* | 10/2005 | Loyer | G06F 17/5036 702/57 |
| 2006/0167651 A1* | 7/2006 | Zangooie | G01B 11/0625 702/179 |
| 2008/0106728 A1* | 5/2008 | Vuong et al. | 356/73 |
| 2008/0106729 A1* | 5/2008 | Vuong et al. | 356/73 |
| 2008/0170241 A1* | 7/2008 | Chard | H01L 22/12 356/625 |
| 2010/0175033 A1 | 7/2010 | Adel et al. | |
| 2010/0322000 A1 | 12/2010 | Shim et al. | |

\* cited by examiner

SECONDARY TARGET DESIGN FOR OPTICAL MEASUREMENTS

PRIORITY

The present application claims priority to U.S. Provisional Application Ser. No. 61/555,108, entitled METHOD OF OPTIMIZING OPTICAL CRITICAL DIMENSION MEASUREMENTS THROUGH SECONDARY TARGET DESIGN, By Sungchul Yoo et al., filed Nov. 3, 2011, or is an application of which a currently co-pending application is entitled to the benefit of the filing date.

TECHNICAL FIELD

The present disclosure generally relates to the field of optical metrology and more particularly to a method of improving optical measurements with secondary target design.

BACKGROUND

Semiconductors are continually being fabricated on smaller scales as technology moves forward. Measurement techniques must similarly evolve so that tighter device specifications can be properly monitored and maintained. Currently, samples are often measured utilizing metrology techniques, such as ellipsometry, reflectometry, and the like. Scatterometry models may be utilized to fit data collected from a measurement target of the sample to determine sample parameters at higher degrees of precision and accuracy.

Three dimensional memory stacks and other multiple layer samples may have repeating structures with high correlation between parameters characterizing multiple layers, deep contact holes, and other challenging structural attributes. The complex sample structures tend to make it difficult to determine sample parameters with a high degree of accuracy and precision. Multiple tool or multiple target measurement techniques may be employed to improve sensitivity to complex sample parameters. However, data collected from multiple tools or multiple targets continues to be limited by structural uncertainties.

SUMMARY

The present disclosure is directed to designing at least one secondary target to increase sensitivity and/or reduce correlation for at least one selected parameter of a primary target.

One embodiment of the present disclosure is a system for analyzing at least one sample. The system may include a sample stage configured to receive at least one sample. The system may further include at least one illumination source configured to illuminate at least one portion of the sample. The system may further include at least one detector configured to receive illumination reflected from the illuminated portion of the sample. The system may further include a computing system communicatively coupled to the at least one detector. The computing system may be configured to receive a primary set of parameters of a primary target of the sample from the detector. The computing system may be further configured to receive a secondary set of parameters of at least one secondary target of the sample from the detector. The secondary target may include at least one controlled parameter configured for increasing sensitivity of at least one selected parameter of the primary target and/or reducing correlation of at least one selected parameter of the primary target with other parameters of the primary target. The secondary target may further include at least one parameter in common with the primary target. The computing system may be further configured to prepare a scatterometry model utilizing the primary set of parameters and the secondary set of parameters. The computing system may be further configured to determine at least one parameter of the at least one sample utilizing the prepared scatterometry model.

Another embodiment of the present disclosure is a method of designing a secondary target. The method may include the steps of: receiving a primary set of parameters of a primary target of at least one sample; selecting at least one parameter of the primary target; receiving a secondary set of parameters of a secondary target of the at least one sample; controlling at least one parameter of the secondary target to increase sensitivity and/or reduce correlation of the selected parameter of the primary target; preparing a scatterometry model utilizing the primary set of parameters and the secondary set of parameters; determining a level of sensitivity or a level of correlation for the at least one selected parameter of the primary target utilizing the scatterometry model; and modifying the at least one controlled parameter of the secondary target until a selected level of sensitivity or a selected level of correlation is achieved.

In a further embodiment, at least one parameter of the secondary target is controlled to increase sensitivity and/or reduce correlation of at least one selected parameter of the primary target by at least one of the following: modifying a critical dimension of the secondary target to a selected critical dimension value; modifying pitch of the secondary target to a selected pitch value; modifying device layout of the secondary target to a selected device layout; modifying thickness of at least one film stack of the secondary target to a selected thickness value; adding at least one film layer to the secondary target; or removing at least one film layer from the secondary target.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1A:
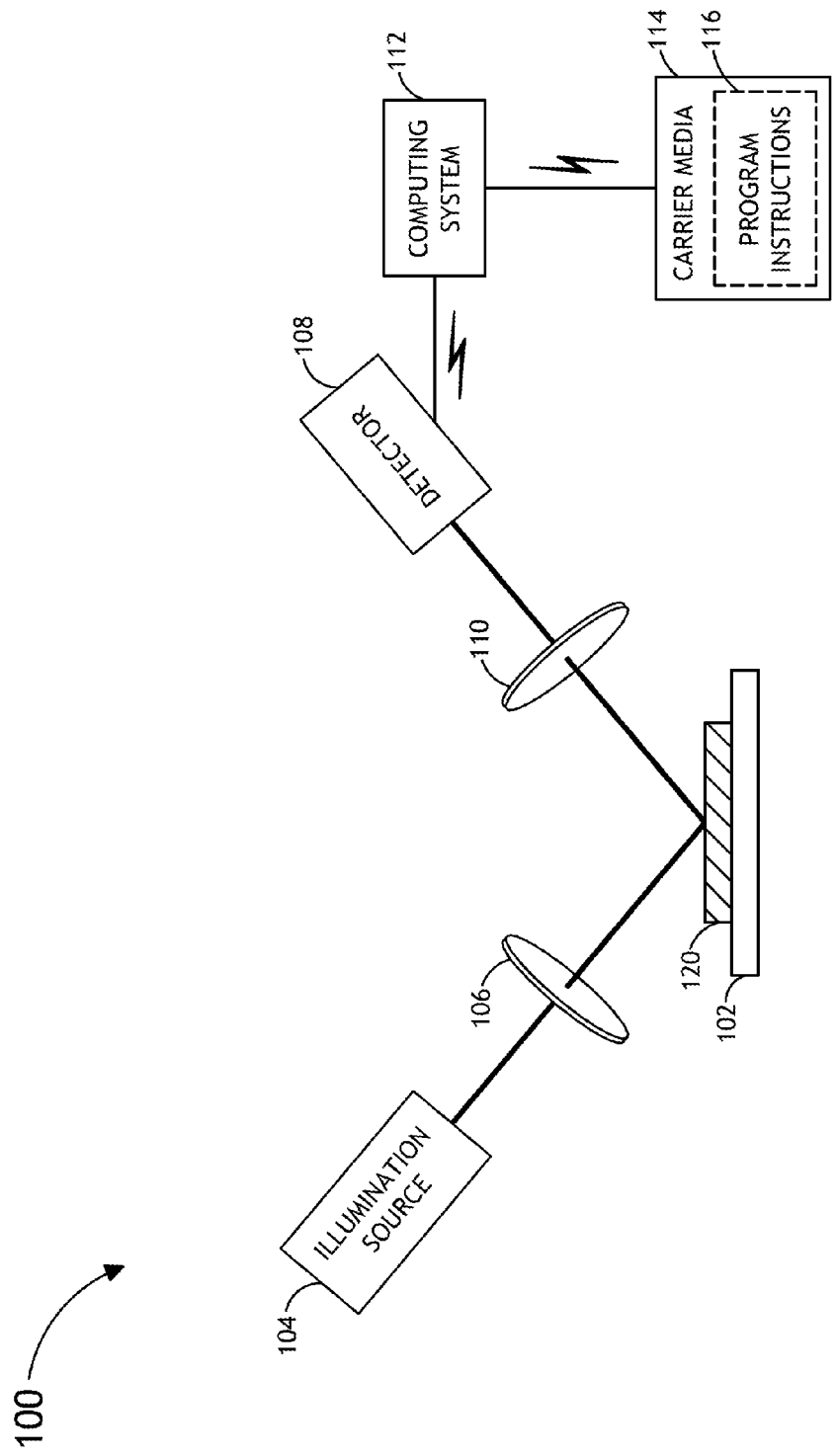
FIG. 1A is a block diagram illustrating a system for analyzing at least one sample, in accordance with an embodiment of this disclosure.
Figure 1B:
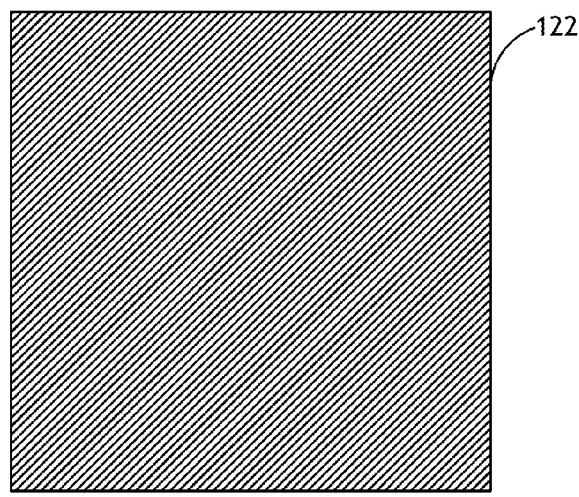
FIG. 1B is a conceptual illustration of secondary target designs, wherein the secondary target includes an unpatterned film or a patterned film, in accordance with various embodiments of this disclosure.
Figure 1B:
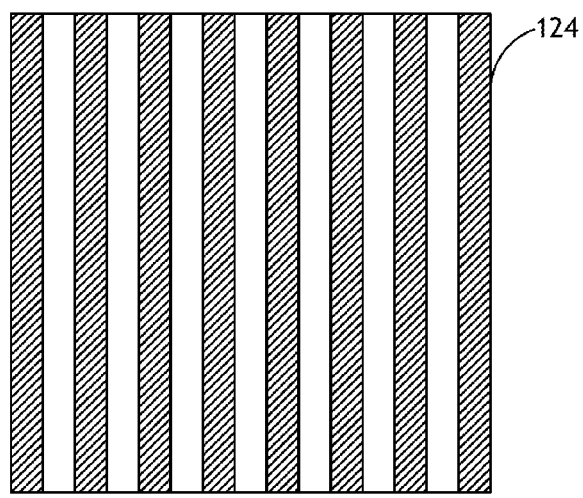
Figure 1C:
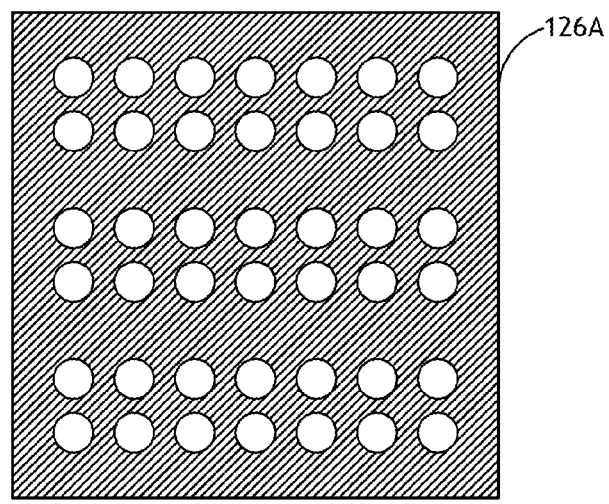
FIG. 1C is a conceptual illustration of a secondary target design, wherein the secondary target includes a patterned film with a plurality of contact holes or trenches, in accordance with an embodiment of this disclosure.
Figure 1C:
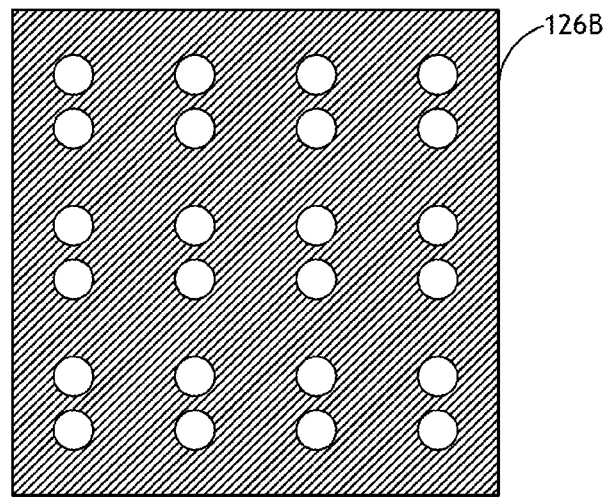
Figure 2:
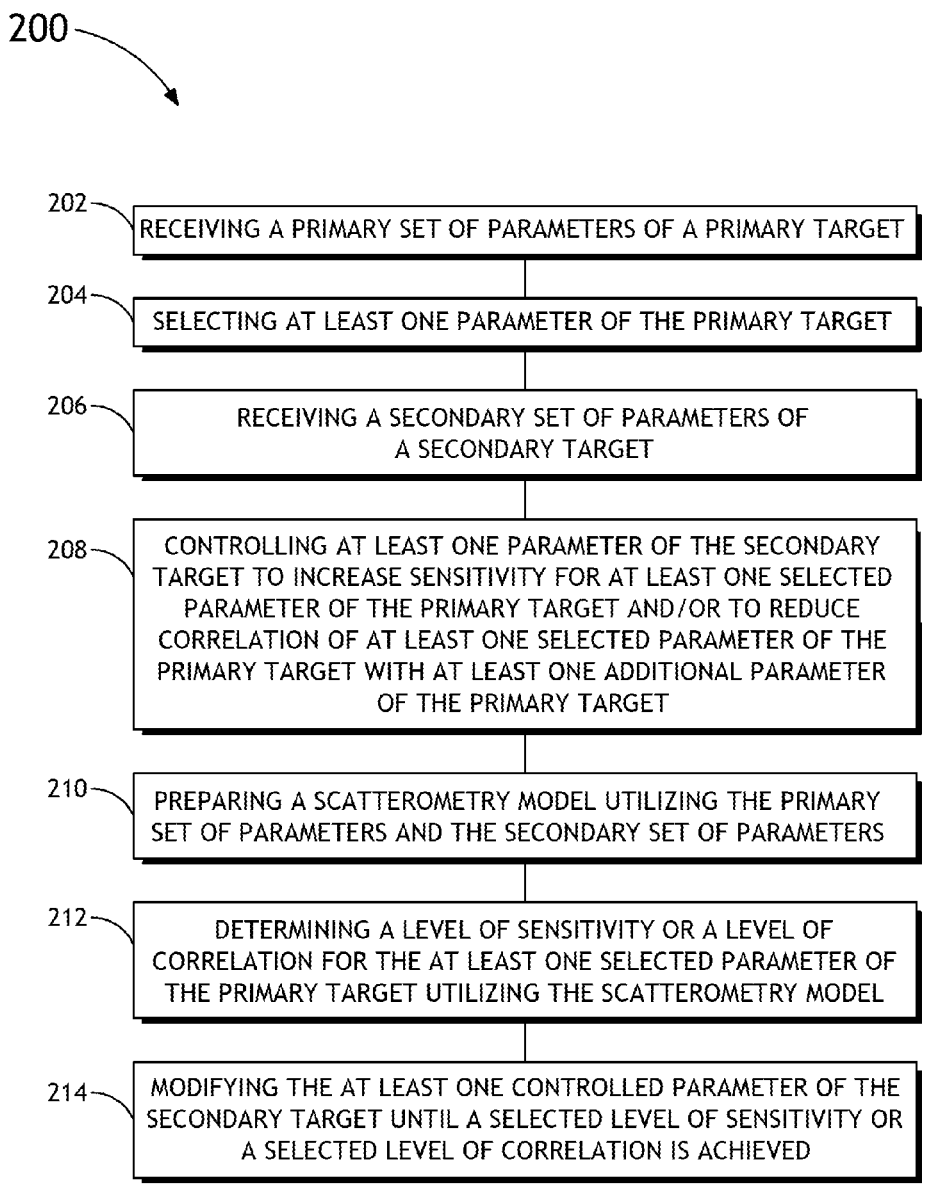
FIG. 2 is a flow diagram illustrating a method of designing a secondary target, in accordance with an embodiment of this disclosure.

FIGS. 1A through 2 generally illustrate a system and method for analyzing a sample to determine at least one parameter of the sample or of one or more layers of the sample (hereinafter "sample parameter"). For example, sample parameters may include thickness, crystallinity, composition, critical dimension, line spacing, line width, wall depth, wall profile, and the like. Complex samples may have parameters with low sensitivity or structural attributes, such as highly correlated repeating layers or deep contact holes, which decrease measurement certainty for various sample parameters. For example, a multiple layer sample may include a three dimensional memory stack, commonly used for TCAT or BICS based memory devices. U.S. Pat. No. 7,478,019, incorporated herein by reference, discusses an approach for improving measurement sensitivity utilizing data collected from multiple tools or multiple targets to determine at least one sample parameter of interest. A method of designing at least one secondary target to improve sensitivity and/or reduce correlation for at least one selected parameter of a primary target is further provided herein.

As used throughout the present disclosure, the term "sample" generally refers to a substrate formed of a semiconductor or non-semiconductor material including one or more "layers" or "films", and patterned structures which are usually chosen to be periodic for optical metrology. For example, semiconductor or non-semiconductor materials include, but are not limited to, monocrystalline silicon, gallium arsenide, and indium phosphide. Layers formed on the substrate may include, but are not limited to, a resist, a dielectric material, a conductive material, or a semiconductive material. Many different types of sample layers are known in the art, and the term sample as used herein is intended to encompass a substrate and any types of layers formed thereon.

FIG. 1A illustrates a system 100 for analyzing at least one sample 120 to determine at least one sample parameter of interest, in accordance with an embodiment of this disclosure. The embodiment of system 100 shown in FIG. 1A includes a generic ellipsometry system for illustrative purposes only. However, the system 100 may include any metrology system known to the art, such as spectroscopic ellipsometry systems, reflectometry systems, angle-resolved reflectometry systems, and the like. In some embodiments, the system 100 may include, but is not limited to, any of the metrology tools or systems discussed in U.S. Pat. Nos. 5,607,800, 5,867,276, 5,963,329, 5,739,909, 5,889,593, 6,429,943, 6,819,426, and 6,813,034, all included herein by reference.

The system 100 may include a sample stage 102 configured to receive and support the sample 120. In one embodiment, the sample stage 102 may be further configured to actuate the sample 120 to a selected location. For example, an actuator, such as a motor or gear, mechanically coupled to the sample stage 102 may be configured to rotate or translate the sample stage 102 to actuate the sample 120. Alternatively, a contactless actuator, such as a magnetic suspension mechanism, may be configured to actuate the sample stage 102.

The system 100 may further include at least one illumination source 104 configured to provide illumination along an illumination path to illuminate at least one portion of the sample 120. The illumination path may include a direct line of sight between the illumination source 104 and the sample 120. Alternatively, the illumination path may be delineated by an arrangement of one or more optical elements, such as retarders, quarter wave plates, focus optics, phase modulators, polarizers, mirrors, beam splitters, prisms, reflectors, converging/diverging lenses, and the like. The system 100 may include one or more illumination optics 106 disposed along the illumination path. The illumination optics 106 may be configured to filter, focus, attenuate, and/or modulate illumination transferred along the illumination path to the illumination portion of the sample 120. For example, the illumination optics 106 may include a polarizer and a focusing lens configured, respectively, to polarize and focus illumination delivered to the illuminated portion of the sample 120.

The system 100 may further include at least one detector 108 configured to receive at least a portion of illumination reflected from the illuminated portion of the sample 120. Illumination reflected from the illuminated portion of the sample 120 may be directed to the detector 108 along a detection path. The detection path may include a direct line of sight between the detector 108 and the illuminated portion of the sample 120. Alternatively, the detection path may be delineated by one or more optical elements, as was previously discussed with regards to the illumination path. The system 100 may further include one or more detection optics 110 disposed along the detection path for filtering, focusing, attenuating, and/or modulating illumination reflected from the illuminated portion of the sample 120. For example, the detection optics 110 may include an analyzer and a delivery lens configured, respectively, to polarize and focus reflected illumination delivered to the detector 108. The foregoing embodiments of system 100 are included for illustrative purposes only and should not be construed to limit the present disclosure in any way. Furthermore, it is contemplated that the system 100 may include any number of illumination sources 104, detectors 108, or optics 106, 110 arranged in any metrology configuration known to the art.

The system 100 may further include at least one computing system 112 communicatively coupled to the one or more detectors 108. The computing system 112 may include at least one processor configured to execute program instructions 116 from carrier media 114, such as a hard disk drive, solid state disk, flash memory, random access memory, an optical disk, magnetic tape, or any other permanent or semi-permanent data storage medium now or hereafter known to the art. The computing system 112 may be configured to receive data associated with illumination received by the detector 108. Data received from the detector 108 may include information associated with one or more sample parameters determined utilizing illumination reflected from the illuminated portion of the sample 120.

Referring to FIGS. 1B and 1C, one or more samples 120 may include a plurality of targets. For example, the sample 120 may include a primary target and at least one secondary target. Alternatively, the primary and secondary targets may be located on separate samples 120. The primary and secondary targets may include, but are not limited to, one or more unpatterned films 122 or one or more patterned films 124, 126A, 126B. The secondary target may have selected structural attributes including, but not limited to, structural attributes described in the following embodiments. In one embodiment, the secondary target may include one or more unpatterned films 122 with all the layers present. In another embodiment, the secondary target may include one or more unpatterned films 122 that are partially etched. In another embodiment, the secondary target may include one or more patterned films 124, 126A, 126B with periodic features such as, but not limited to, lines, trenches, or contact holes. In an exemplary embodiment, the secondary target may include one or more patterned films with a plurality of two dimensional line space gratings 124. In another exemplary embodiment, the secondary target may include one or more patterned films with a plurality of contact holes or trenches 126A differing in pitch from a plurality of contact holes or trenches 126B of the primary target.

The primary target and at least one secondary target may further include at least one common parameter. The secondary target may further include at least one controlled parameter. The controlled parameter may include, but is not limited to, critical dimension, pitch, device layout, film stack thickness, or number of film layers. In an embodiment, modifications to the controlled parameter may increase sensitivity to at least one selected parameter of the primary target. In another embodiment, modifications to the controlled parameter may reduce correlation between the selected parameter and other parameters of the primary target. In some embodiments, controlling parameters of the secondary target may further allow for a combination of increased sensitivity and reduced correlation for the selected parameter of the primary target.

In one embodiment, the computing system 112 may be configured to receive a set of one or more parameters (i.e. the "primary set" of parameters) of the primary target of the sample 120, including the selected parameter. The computing system 112 may be further configured to receive a set of one or more parameters (i.e. the "secondary set" of parameters) of the secondary target of the sample 120, including the controlled parameter. The computing system 112 may be further configured to prepare a scatterometry model utilizing the primary set of parameters and the secondary set of parameters. The computing system 112 may be configured to incorporate the primary set of parameters and the secondary set of parameters into the scatterometry model utilizing feed forward processing, feed sideways processing, multi-target parallel processing, or any other data conditioning technique known to the art. The scatterometry model may include any analytical, numerical, or mathematical model known to the art for modeling one or more metrology parameters. For example, the scatterometry model may include RCWA algorithms and/or associated data fitting or optimization algorithms. It is noted herein that the foregoing example is included for illustrative purposes only and should not be construed as a limitation of the present disclosure.

The computing system 112 may be further configured to determine a level of sensitivity or a level of correlation for the selected parameter of the primary target utilizing the scatterometry model. The controlled parameter of the secondary target may be adjusted until it is determined that a selected level of sensitivity or a selected level of correlation has been achieved for the selected parameter of the primary target. The computing system 112 may be further configured to determine at least one parameter of the sample 120 utilizing the scatterometry model. The computing system 112 may be further configured to execute one or more steps of method 200 described herein.

FIG. 2 illustrates a method 200 of designing at least one secondary target to improve sensitivity to at least one selected parameter of a primary target of at least one sample and/or reduce correlation between the selected parameter and one or more additional parameters of the primary target. At step 202, a primary set of one or more parameters of a primary target is received. At step 204, at least one parameter of the primary target is selected. In one embodiment, the selected parameter may include a highly correlated parameter and/or a parameter having sensitivity below a selected level. Parameters with low sensitivity and highly correlated parameters tend to cause measurement uncertainty. Measurement certainty may be improved by selectively designing at least one secondary target to increase sensitivity and/or reduce correlation between parameters.

At step 206, a secondary set of one or more parameters of a secondary target is received. At step 208, at least one parameter of the secondary target is controlled to increase sensitivity to the selected parameter of the primary target and/or reduce correlation between the selected parameter and at least one additional parameter of the primary target. Any number of secondary targets may be used. Furthermore, in some embodiments, the secondary target may include a controlled version of the primary target measured at a secondary point in time preceding or succeeding measurement of the primary target. In another embodiment, the secondary target may include the primary target measured utilizing a secondary metrology system or tool. In another embodiment, the primary set of parameters may be obtained from the primary target utilizing a first metrology technology (e.g. spectroscopic ellipsometry), and the secondary set of parameters may be obtained from the secondary target utilizing a second metrology technology (e.g. reflectometry), wherein the second technology is different from the first. Furthermore, the secondary target design may be based upon characteristics or features of the second metrology system. Any mention of the secondary target herein is intended to encompass any of the foregoing secondary targets.

In one embodiment, a critical dimension of the secondary target may be adjusted to a selected value. In another embodiment, the pitch of a plurality of lines, trenches, contact holes, or other periodic features of the secondary target may be modified to a selected value. In another embodiment, the device layout of the secondary target may be modified to a selected device layout. In another embodiment, thickness of at least one film stack of the secondary target may be modified to a selected thickness value. In another embodiment, one or more film layers may be added to or removed from the secondary target. Alternative parameters of one or more secondary targets, beyond those listed herein, may be controlled at step 208 to reduce correlation between parameters of the primary target, increase sensitivity to one or more selected parameters, improve precision or accuracy metrics, and/or achieve selected measurement behavior. In addition, one or more parameters of the primary and secondary targets may be held in common to constrain the fitted data in the prepared model and reduce correlation between model parameters.

At step 210, parameter sets of the primary and secondary targets may be fit into a scatterometry model. In one embodiment, the parameters of the primary and secondary targets may be incorporated to the scatterometry model utilizing feed forward or feed sideways processing. The secondary set of parameters may be fit into a secondary scatterometry model. Results from the secondary model may be fed into the scatterometry model for the primary target. In feed forward processing, the parameters of the secondary target may include parameters of the primary target at an earlier point in time. In another embodiment, the parameters may be incorporated utilizing multi-target processing. In multi-target processing, the primary set of parameters and the secondary set of parameters may be fit into respective models with a subset of parameters held in common while the models are simultaneously optimized in parallel.

At step 212, simulations utilizing the scatterometry model may be conducted to determine a level of sensitivity or a level of correlation for the selected parameter of the primary target. At step 214, one or more controlled parameters of the secondary target may be manipulated until it is determined that a selected level of sensitivity to the selected parameter is achieved and/or correlation between the selected parameter and other parameters is reduced to a selected level of correlation. Optical simulations may be performed to test for optical sensitivity utilizing information associated with near optical field spatial distribution as a function of wavelength, angle of incidence, and polarization to guide secondary target design. For example, one or more controlled parameters of the secondary target may be modified in response to near field intensity enhancement or rate of change. In another embodiment, the controlled parameter or a selected value of the controlled parameter may be determined utilizing eigenmodes, such as waveguide modes in multiple layers. One or more controlled parameters of the secondary target may be manipulated for supporting one or more eigenmodes to achieve selected sensitivity and/or reduce correlation between parameters of the scatterometry model.

Two dimensional (2D) and/or three dimensional (3D) secondary targets may be utilized to assist measurement of one or more selected parameters of the primary target. In an exemplary embodiment, the primary target may include a Fin height in 3D FinFet where Fin height sensitivity is low. A 2D secondary target may be designed to increase sensitivity to a selected parameter having low sensitivity, such as oxide trench height. The 2D secondary target may be incorporated with parameters of the 3D primary target to allow for more accurate and robust measurements.

In another exemplary embodiment, the primary target may include an isolated lithography structure having a high correlation among parameters, making it difficult to determine middle CD, HT, and SWA. A secondary target that is denser than the isolated lithography structure of the primary target may be utilized to reduce correlation, thereby allowing simultaneous determination of the CD, HT, and SWA parameters.

It is contemplated that each of the embodiments of the method described above may include any other step(s) of any other method(s) described herein. In addition, each of the embodiments of the method described above may be performed by any of the systems described herein.

It should be recognized that the various steps described throughout the present disclosure may be carried out by a single computing system or by multiple computing systems. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

The computing system may include, but is not limited to, a personal computing system, mainframe computing system, workstation, image computer, parallel processor, or any other device known in the art. In general, the term "computing system" may be broadly defined to encompass any device having one or more processors, which execute instructions from a memory medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for analyzing at least one sample, comprising:
   a sample stage configured to receive at least one sample;
   at least one illumination source configured to illuminate at least one portion of the at least one sample;
   at least one detector configured to receive illumination reflected from the at least one illuminated portion of the at least one sample; and
   a computing system communicatively coupled to the at least one detector, the computing system configured to:
      receive a primary set of parameters of a primary target of the at least one sample from the at least one detector;
      receive a secondary set of parameters of a secondary target of the at least one sample from the at least one detector, the secondary target including at least one parameter in common with the primary target, the secondary target further including at least one controlled parameter configured for at least one of: increasing sensitivity for at least one selected parameter of the primary target; or reducing correlation of at least one selected parameter of the primary target with at least one additional parameter of the primary target;
      prepare a scatterometry model utilizing the primary set of parameters and the secondary set of parameters; and
      determine at least one parameter of the at least one sample utilizing the scatterometry model.

2. The system of claim 1, wherein the at least one controlled parameter of the secondary target includes at least one of:
   critical dimension, pitch, device layout, film stack thickness, or number of film layers.

3. The system of claim 1, wherein the computing system is further configured to prepare the scatterometry model utilizing at least one of:
   feed forward processing, feed sideways processing, or multi-target processing.

4. The system of claim 1, wherein the at least one sample includes a FinFET structure.

5. The system of claim 1, wherein the at least one sample includes an isolated lithography structure.

6. The system of claim 1, wherein the system is configured for at least one of:
   spectroscopic ellipsometry, reflectometry, or angle-resolved reflectometry.

7. The system of claim 1, wherein the system is configured for obtaining the primary set of parameters of the primary target utilizing a first metrology technology, wherein the system is further configured for obtaining the secondary set of parameters of the secondary target utilizing a second metrology technology, wherein the second metrology technology is different from the first metrology technology.

8. The system of claim 1, wherein the secondary target of the at least one sample includes one or more unpatterned films.

9. The system of claim 8, wherein the one or more unpatterned films are partially etched.

10. The system of claim 1, wherein the at least one sample includes a three dimensional memory stack.

11. The system of claim 10, wherein the three dimensional memory stack includes at least one of:
a TCAT memory stack or a BIOS memory stack.

12. The system of claim 1, wherein the secondary target of the at least one sample includes one or more patterned films.

13. The system of claim 12, wherein the one or more patterned films include a plurality of line-space gratings.

14. The system of claim 12, wherein the one or more patterned films include a plurality of contact holes.

15. The system of claim 12, wherein the one or more patterned films include a plurality of trenches.

16. A method of designing at least one secondary target, comprising:
receiving a primary set of parameters of a primary target of at least one sample;
selecting at least one parameter of the primary target;
receiving a secondary set of parameters of a secondary target of the at least one sample;
controlling at least one parameter of the secondary target for at least one of: increasing sensitivity for the at least one selected parameter of the primary target; or reducing correlation of the at least one selected parameter of the primary target with at least one additional parameter of the primary target;
preparing a scatterometry model utilizing the primary set of parameters and the secondary set of parameters;
determining a level of sensitivity or a level of correlation for the at least one selected parameter of the primary target utilizing the scatterometry model; and
modifying the at least one controlled parameter of the secondary target until a selected level of sensitivity or a selected level of correlation is achieved.

17. The method of claim 16, wherein the at least one controlled parameter of the secondary target includes at least one of:
critical dimension, pitch, device layout, film stack thickness, or number of film layers.

18. The method of claim 16, wherein preparing the scatterometry model includes utilizing at least one of:
feed forward processing, feed sideways processing, or multi-target processing.

19. The method of claim 16, wherein the at least one sample includes a three dimensional memory stack.

20. The method of claim 16, wherein the three dimensional memory stack includes at least one of:
a TCAT memory stack or a BIOS memory stack.

21. The method of claim 16, wherein the at least one sample includes a FinFET structure.

22. The method of claim 16, wherein the at least one sample includes an isolated lithography structure.

23. The method of claim 16, wherein the primary set of parameters or the secondary set of parameters are obtained utilizing at least one of:
a spectroscopic ellipsometry system, a reflectometry system, or an angle-resolved reflectometry system.

24. The method of claim 16, wherein the primary set of parameters of the primary target is obtained utilizing a first metrology technology, wherein the secondary set of parameters of the secondary target is obtained utilizing a second metrology technology, wherein the second metrology technology is different from the first metrology technology.

25. The method of claim 16, wherein the secondary target of the at least one sample includes one or more unpatterned films.

26. The method of claim 25, wherein the one or more unpatterned films are partially etched.

27. The method of claim 16, wherein the secondary target of the at least one sample includes one or more patterned films.

28. The method of claim 27, wherein the one or more patterned films include a plurality of line-space gratings.

29. The method of claim 27, wherein the one or more patterned films include a plurality of contact holes.

30. The method of claim 27, wherein the one or more patterned films include a plurality of trenches.

31. A method of designing at least one secondary target, comprising:
receiving a primary set of parameters of a primary target of at least one sample;
selecting at least one parameter of the primary target;
receiving a secondary set of parameters of a secondary target of the at least one sample; and
controlling at least one parameter of the secondary target for at least one of: increasing sensitivity for the at least one selected parameter of the primary target; or reducing correlation of the at least one selected parameter of the primary target with at least one additional parameter of the primary target, wherein controlling the at least one parameter includes at least one of:
modifying a critical dimension of the secondary target to a selected critical dimension value;
modifying pitch of the secondary target to a selected pitch value;
modifying device layout of the secondary target to a selected device layout;
modifying thickness of at least one film stack of the secondary target to a selected thickness value;
adding at least one film layer to the secondary target; or
removing at least one film layer from the secondary target.

32. The method of claim 31, wherein the method further includes:
preparing a scatterometry model utilizing the primary set of parameters and the secondary set of parameters;
determining a level of sensitivity or a level of correlation for the at least one selected parameter of the primary target utilizing the scatterometry model; and
modifying the at least one controlled parameter of the secondary target until a selected level of sensitivity or a selected level of correlation is achieved.

* * * * *